(12) United States Patent
Wolf (10) Patent No.: US 6,232,130 B1
(45) Date of Patent: May 15, 2001

(54) METHOD FOR DETECTING OR QUANTIFYING CARBOHYDRATE CONTAINING COMPOUNDS

(75) Inventor: David E. Wolf, Hudson, MA (US)

(73) Assignee: Sensor Technologies, Inc., Shrewsbury, MA (US)

( * ) Notice: Subject to any disclaimer, the term of this patent is extended or adjusted under 35 U.S.C. 154(b) by 0 days.

(21) Appl. No.: 09/090,601

(22) Filed: Jun. 4, 1998

Related U.S. Application Data (60) Provisional application No. 60/048,512, filed on Jun. 4, 1997.

(51) Int. Cl.[7] .................. G01N 33/566; G01N 33/53; G01N 33/00; A61K 49/00
(52) U.S. Cl. ............... 436/501; 436/14; 436/147; 436/164; 436/172; 436/95; 436/531; 436/545; 436/546; 436/805; 436/807; 436/815; 436/827; 435/7; 435/7.1; 435/7.93; 435/14; 424/9
(58) Field of Search .................. 436/14, 164, 172, 436/147, 501, 95, 531, 545, 546, 805, 807, 815, 827; 435/7, 14, 7.93, 7.1; 424/9

(56) References Cited

U.S. PATENT DOCUMENTS 5,342,789   8/1994   Chick et al. ............ 436/501

FOREIGN PATENT DOCUMENTS

| WO 90-US7519 | * 12/1990 | (WO) .................. 436/501 |
| WO 94/00602 | 1/1994 | (WO) . |
| WO 96/28029 | 9/1996 | (WO) . |
| PCT/US98/11546 | 6/1998 | (WO) . |

OTHER PUBLICATIONS

Kohnken et al., Affinity labeling of the carbohydrate binding site of the lectin discoidin I using a photoactivatable radio-iodinated monosaccharide, Biochemistry 26(26): 8727–8735 (1987).*
Beppu et al., J. Biochem. 78:1013–1019 (1975) Photoaffinity Labeling of Concanaval in A.
Beppu et al., J. Biochem. 79:1113–1117 (1976) Preparation of Monovalent Succinyl–concanaval in A and Its Mitogenic Activity.
Clegg, Robert M., Current Opinion in Biotechnology 6:103–110 (1995) Fluorescence resonance energy transfer.
Fraser et al., PNAS 73:790–794 (1976) Monovalent derivatives of concanaval in A.
Gunther et al., PNAS 70:1012–1016 (1973) Concanaval in A Derivatives with Altered Biological Activities.
Lakowicz et al., Analytica Chimica Acta 271:155–164 (1993) Optical sensing of glucose using phase–modulation fluorimetry.
Tanaka et al., J. Biochem. 89:1643–1646 (1981) Monovalent Monomer Derivative of Concanaval in A Produced.

(List continued on next page.)

Primary Examiner—Long V. Le
Assistant Examiner—Gailene R. Gabel
(74) Attorney, Agent, or Firm—Fish & Richardson P.C.

(57) ABSTRACT

A method of evaluating a carbohydrate in a sample. The method includes providing a low valency carbohydrate binding ligand, providing a glycoconjugate which includes a label, and a carbohydrate moiety, contacting the low valency carbohydrate binding ligand and the glycoconjugate with the sample, determining the extent of binding of the low valency carbohydrate binding ligand with the glycoconjugate, the binding of the low valency carbohydrate binding ligand with the glycoconjugate being correlated with the amount of carbohydrate in the sample.

17 Claims, 6 Drawing Sheets

OTHER PUBLICATIONS

Wands et al., PNAS 73:2118–2122 (1976) Mechanism of human lymphocyte stimulation by conanaval in A: Role of valence and surface binding sites.

Wang et al., J. Biol. Chem. 250:1490–1502 (1975) The Covalent and Three-Dimensional Structure of Concanaval in A.

* cited by examiner

METHOD FOR DETECTING OR QUANTIFYING CARBOHYDRATE CONTAINING COMPOUNDS

This application is a continuation-in-part and claims priority from. U.S. Provisional Patent application serial No. 60/048,512, filed on Jun. 4, 1997.

BACKGROUND OF THE INVENTION

The invention relates to the use of low valency carbohydrate binding ligands to evaluate a carbohydrate in a sample, e.g., using such ligands with fluorescence resonance energy transfer (FRET) to measure carbohydrate, e.g., free carbohydrate or a carbohydrate of a carbohydrate containing compound.

SUMMARY OF THE INVENTION

In general, the invention features, a method of evaluating a carbohydrate in a sample. The method includes:

providing a low valency carbohydrate binding ligand, providing a glycoconjugate, which preferably includes a label, and a carbohydrate moiety, contacting the low valency carbohydrate binding ligand and the glycoconjugate with the sample, determining the extent of binding of the low valency carbohydrate binding ligand with the glycoconjugate the binding of the low valency carbohydrate binding ligand with the glycoconjugate being correlated with the amount of carbohydrate in the sample.

The label, when present, can be any substance which allows detection of the glycoconjugate, e.g., a radioactive label, a fluorescent label, an enzyme, a proximity-based signal generating label moiety, e.g., a FRET component, a homogeneous time resolved fluorescence (HTRF) component, a luminescent oxygen channeling assay (LOCI) component, biotin or avidin or other functionally similar substances, an antibody moiety recognized by an antibody or an antibody, or an antigen binding portion of antibody.

In preferred embodiments, the evaluation is made in the presence of the glycoconjugate displaced by the carbohydrate and the low valency carbohydrate binding ligand reversibly bound to the carbohydrate.

In preferred embodiments, the sample includes a body fluid; a urine sample; a blood sample; a plasma sample; intracellular fluid; interstitial fluid; or a cell homogenate or extract.

In preferred embodiments, the method measures the concentration of glucose in a sample which includes subcutaneous body fluids, intracutaneous body fluid, or blood.

In preferred embodiments, the carbohydrate analyte is a monosaccharide; a disaccharide; a polysaccharide; glucose; a carbohydrate which is a component of another molecule or supramolecular structures, e.g., a macromolecule, e.g., a carbohydrate moiety of a glycoprotein.

In preferred embodiments, the glycoconjugate includes one or more glycosylated serum albumin, preferably human or bovine, capable of binding to low valency carbohydrate binding ligands.

In preferred embodiments, the low valency carbohydrate binding ligand is a lectin, e.g., reduced valency Concanavalin A.

In preferred embodiments, the low valency carbohydrate binding ligand and the glycoconjugate bind reversibly.

In preferred embodiments, the low valency carbohydrate binding ligand and the glycoconjugate bind reversibly over the range of carbohydrate concentrations found in body fluids; physiological concentrations of carbohydrate in the body fluid being tested, e.g., 0.05 mg/ml to 5.0 mg/ml or 0.5 mg/ml to 5 mg/ml of carbohydrates, e.g., glucose.

In another aspect, the invention features, a method of evaluating a carbohydrate in a sample. The method includes the steps of:

a) contacting the sample with a specific binding pair which includes a first binding member and a second binding member, wherein the first binding member includes a low valency carbohydrate binding ligand coupled to a first energy absorbing FRET component, wherein the second binding member is a glycoconjugate which includes a carbohydrate and a second energy absorbing FRET component, wherein the excited state energy level of the first energy absorbing FRET component overlaps with the excited state energy level of the second energy absorbing FRET component, and wherein the low valency carbohydrate binding ligand and the glycoconjugate can reversibly bind to each other such that carbohydrate present in the sample can displace the glycoconjugate and can reversibly bind to the low valency carbohydrate binding ligand; and b) evaluating the extent to which non-radiative fluorescence resonance energy transfer occurs between the first energy absorbing FRET component and the second energy absorbing FRET component, thereby evaluating the carbohydrate in the sample.

In preferred embodiments, the evaluation is made in the presence of the glycoconjugate displaced by the carbohydrate and the low valency carbohydrate binding ligand reversibly bound to the carbohydrate.

Energy transfer can, by way of example, be evaluated by measuring one or more of: donor quenching, donor lifetime, e.g., decrease in donor excited lifetime, sensitized acceptor emission, fluorescence depolarisation. It can also be measured by determining the ratio of two parameters, e.g., the ratio of a donor parameter to an acceptor parameter, e.g., the ratio of donor to acceptor fluorescence, or depolarization of fluorescence relative to excitation.

In preferred embodiments, the evaluation includes measuring energy transfer as a function of fluorescence intensities of the first energy absorbing FRET component and the second energy absorbing FRET component.

In preferred embodiments, the method includes comparing the result of step (b) with a FRET value obtained from a calibration step.

In preferred embodiments, the sample includes a body fluid; a urine sample; a blood sample; a plasma sample; intracellular fluid; interstitial fluid; or a cell homogenate or extract.

In preferred embodiments, the method measures the concentration of glucose in a sample which includes subcutaneous body fluid, intracutaneous body fluid, or blood.

In preferred embodiments, the carbohydrate analyte is a monosaccharide; a disaccharide; a polysaccharide; glucose; a carbohydrate which is a component of another molecule or supramolecular structures, e.g., a macromolecule, e.g., a carbohydrate moiety of a glycoprotein.

In preferred embodiments, the glycoconjugate includes one or more glycosylated serum albumin, preferably human or bovine, capable of binding to low valency carbohydrate binding ligands.

In preferred embodiments, the low valency carbohydrate binding ligand is a lectin, e.g., reduced valency Concanavalin A.

In preferred embodiments, the low valency carbohydrate binding ligand and the glycoconjugate bind reversibly over the range of carbohydrate concentrations found in body fluids; physiological concentrations of carbohydrate in the body fluid being tested, e.g., 0.05 mg/ml to 5.0 mg/ml or 0.5 mg/ml to 5 mg/ml of carbohydrates, e.g., glucose.

In preferred embodiments, first and second energy absorbing FRET component are fluorophores and, at least one of fluorophores is chosen from the group consisting of fluoresceins, rhodamines, BODIPY's, cyanine dyes and phycobiliproteins; the low valency carbohydrate binding ligand is labeled with a fluorophore and the glycoconjugate is labeled with a fluorophore in the non-radiative fluorescence resonance energy transfer process; low valency carbohydrate binding ligand is labeled with a fluorophore which is the acceptor and the glycoconjugate is labeled with a fluorophore which is the donor in the non-radiative fluorescence resonance energy transfer process.

In preferred embodiments, the first member of the specific binding pair is fluorophore-labeled low valency Concanavalin A, the second member of the specific binding pair is fluorophore-labeled glycosylated serum albumin capable of binding to low valency Concanavalin A, and the non-radiative fluorescence resonance energy transfer can be determined by measuring the ratio of the light emissions attributable to the two fluorophores.

In preferred embodiments, the specific binding pair is placed in a microdialysis vessel and then subcutaneously implanted in the subject; the specific binding pair is encapsulated and then subcutaneously implanted in the subject; the specific binding pair is mixed with a carrier, e.g., an oil into which glucose can pass and then implanted, e.g., injected subcutaneously, in the subject; the specific binding pair is tattooed into the skin of the subject; the components of the specific binding pair are chemically modified to enable them to bind to the cells of the subject; the specific binding pair is bound to a solid support which is then implanted in the subject, the support retaining the specific binding pair at the desired location once implanted in the subject; or at least one member of the specific binding pair is provided on a solid support, useful e.g., for repeatedly contacting body fluid samples; the specific binding pair is provided on a support having a membrane positioned thereon in such a manner that is covers the specific binding pair, the membrane having a pore size which prevents passage of the specific binding pair from the support to the body fluid but permits passage of carbohydrate between the body fluid and the support.

In preferred embodiments, the specific binding pair is encapsulated in an immunoisolating capsule or microcapsule. For example, the specific binding pair can be encapsulated in a hydrogel core, e.g., an alginate or agarose core which core is surrounded by an immunoisolating membrane, e.g., a polyamino acid membrane, e.g., a polylysine membrane. Composite microcapsules of PCT/US96/03135 are particularly preferred for use with the sensors and methods described herein.

In preferred embodiments, the specific binding pair is illuminated, and the energy transfer is monitored, e.g., through the skin of the subject.

In preferred embodiments, an energy absorbing FRET donor component is coupled to a low valency carbohydrate binding ligand and an energy absorbing FRET acceptor is coupled to the glyconjugate. In other preferred embodiments an energy absorbing FRET acceptor component is coupled to a low valency carbohydrate binding ligand and an energy absorbing FRET donor is coupled to the glycoconjugate.

In another aspect, the invention features, an in-vivo method for determining carbohydrate, e.g., glucose, concentration in a subject. The method includes the steps of:

a) placing a sensor in contact with carbohydrate, e.g., glucose, present in the body fluids of the subject in such a way that once in place the sensor does not exit the skin of the subject, thereby permitting non-invasive monitoring of the carbohydrate, in the body fluids of the subject. The sensor includes a first binding member and a second binding member, wherein the first binding member includes a low valency carbohydrate binding ligand coupled to a first energy absorbing FRET component, wherein the second binding member includes a glycoconjugate which includes a carbohydrate and a second energy absorbing FRET component, wherein the excited state energy level of the first energy absorbing FRET component overlaps with the excited state energy level of the second energy absorbing FRET component, and wherein the low valency carbohydrate binding ligand and the glycoconjugate can reversibly bind to each other such that carbohydrate present in the sample can displace the glycoconjugate and can reversibly bind to the low valency carbohydrate binding ligand;

b) non-invasively monitoring the extent to which non-radiative fluorescence energy transfer occurs between the first energy absorbing FRET component and the second energy absorbing FRET, thereby quantifying the carbohydrate in the subject.

In preferred embodiments, the evaluation is made in the presence of the glycoconjugate displaced by the carbohydrate and the low valency carbohydrate binding ligand reversibly bound to the carbohydrate.

Energy transfer can, by way of example, be evaluated by measuring one or more of: donor quenching, donor lifetime, e.g., decrease in donor excited lifetime, sensitized acceptor emission, fluorescence depolarisation. It can also be measured by determining the ratio of two parameters, e.g., the ratio of a donor parameter to an acceptor parameter, e.g., the ratio of donor to acceptor fluorescence, or depolarization of fluorescence relative to excitation.

In preferred embodiments, the evaluation includes measuring energy transfer as a function of fluorescence intensities of the first energy absorbing FRET component and the second energy absorbing FRET component.

In preferred embodiments, the method includes comparing the result of step (b) with a FRET value obtained from a calibration step.

In preferred embodiments, the method measures the concentration of glucose in the subject's subcutaneous body fluid, intracutaneous body fluid, or blood.

In preferred embodiments, the carbohydrate analyte is, a monosaccharide; a disaccharide; a polysaccharide; glucose; a carbohydrate which is a component of another molecule or supramolecular structures, e.g., a macromolecule, e.g., a carbohydrate moiety of a glycoprotein.

In preferred embodiments, the glycoconjugate includes one or more glycosylated serum albumin, preferably human or bovine, capable of binding to low valency carbohydrate binding ligands.

In preferred embodiments, the low valency carbohydrate binding ligand is a lectin, e.g., reduced valency Concanavalin A.

In preferred embodiments, the low valency carbohydrate binding ligand and the glycoconjugate bind reversibly over the range of carbohydrate concentrations found in body fluids; physiological concentrations of carbohydrate in the body fluid being tested, e.g., 0.05 mg/ml to 5.0 mg/ml or 0.5 mg/ml to 5 mg/ml of carbohydrates, e.g., glucose.

In preferred embodiments, first and second energy absorbing FRET component are fluorophores and, at least one of fluorophores is chosen from the group consisting of fluoresceins, rhodamines, BODIPY's, cyanine dyes and phycobiliproteins; the low valency carbohydrate binding ligand is labeled with a fluorophore and the glycoconjugate is labeled with a fluorophore in the non-radiative fluorescence resonance energy transfer process; low valency carbohydrate binding ligand is labeled with a fluorophore which is the acceptor and the glycoconjugate is labeled with a fluorophore which is the donor in the non-radiative fluorescence resonance energy transfer process.

In preferred embodiments, the first member of the specific binding pair is fluorophore-labeled low valency Concanavalin A, the second member of the specific binding pair is fluorophore-labeled glycosylated serum albumin capable of binding to low valency Concanavalin A, and the non-radiative fluorescence resonance energy transfer can be determined by measuring the ratio of the light emissions attributable to the two fluorophores.

In preferred embodiments, the specific binding pair is placed in a microdialysis vessel and then subcutaneously implanted in the subject; the specific binding pair is encapsulated and then subcutaneously implanted in the subject; the specific binding pair is mixed with a carrier, e.g., an oil into which glucose can pass and then implanted, e.g., injected subcutaneously, in the subject; the specific binding pair is tattooed into the skin of the subject; the components of the specific binding pair are chemically modified to enable them to bind to the cells of the subject; the specific binding pair is bound to a solid support which is then implanted in the subject, the support retaining the specific binding pair at the desired location once implanted in the subject; the specific binding pair is provided on a support having a membrane positioned thereon in such a manner that is covers the specific binding pair, the membrane having a pore size which prevents passage of the specific binding pair from the support to the body fluid but permits passage of carbohydrate between the body fluid and the support.

In preferred embodiments, the sensor is encapsulated in an immunoisolating capsule or microcapsule. For example, the sensor can be encapsulated in a hydrogel core, e.g., an alginate or agarose core which core is surrounded by an immunoisolating membrane, e.g., a polyamino acid membrane, e.g., a polylysine membrane. Composite microcapsules of PCT/US96/03135 are particularly preferred for use with the sensors and methods described herein.

In preferred embodiments, the specific binding pair is illuminated, and the energy transfer is monitored, e.g., through the skin of the subject.

In preferred embodiments, an energy absorbing FRET donor component is coupled to a low valency carbohydrate binding ligand and an energy absorbing FRET acceptor is coupled to the glyconjugate. In other preferred embodiments, an energy absorbing FRET acceptor component is coupled to a low valency carbohydrate binding ligand and an energy absorbing FRET donor is coupled to the glyconjugate.

In another aspect, the invention features a sensor for non-invasively evaluating a carbohydrate, e.g., glucose concentration in a subject. The sensor can be used in-vitro or in-vivo in a subject. The sensor includes a specific binding pair which includes a first binding member and a second binding member, wherein the first binding member includes a low valency carbohydrate binding ligand coupled to a first energy absorbing FRET component, wherein the second binding member includes a glycoconjugate which includes a carbohydrate and a second energy absorbing FRET component, wherein the excited state energy level of the first energy absorbing FRET component overlaps with the excited state energy level of the second energy absorbing FRET component, and wherein the low valency carbohydrate binding ligand and the glycoconjugate can reversibly bind to each other such that carbohydrate present in the sample can displace the glycoconjugate and can reversibly bind to the low valency carbohydrate binding ligand.

In preferred embodiments, the sensor is placed on, in, or under the skin of the subject Energy transfer can, by way of example, be evaluated by measuring one or more of: donor quenching, donor lifetime, e.g., decrease in donor excited lifetime, sensitized acceptor emission, fluorescence depolarisation. It can also be measured by determining the ratio of two parameters, e.g., the ratio of a donor parameter to an acceptor parameter, e.g., the ratio of donor to acceptor fluorescence, or depolarization of fluorescence relative to excitation.

In preferred embodiments, the carbohydrate analyte is a monosaccharide; a disaccharide; a polysaccharide; glucose; a carbohydrate which is a component of another molecule or supramolecular structures, e.g., a macromolecule, e.g., a carbohydrate moiety of a glycoprotein.

In preferred embodiments, the glycoconjugate includes one or more glycosylated serum albumin, preferably human or bovine, capable of binding to low valency glucose binding ligands.

In preferred embodiments, the low valency carbohydrate binding ligand is a lectin, e.g., reduced valency Concanavalin A.

In preferred embodiments, the low valency carbohydrate binding ligand and the glycoconjugate bind reversibly over the range of carbohydrate concentrations found in body fluids; physiological concentrations of carbohydrate in the body fluid being tested, e.g., 0.05 mg/ml to 5.0 mg/ml or 0.5 mg/ml to 5 mg/ml of carbohydrates, e.g., glucose.

In preferred embodiments, first and second energy absorbing FRET component are fluorophores and, at least one of fluorophores is chosen from the group consisting of fluoresceins, rhodamines, BODIPY's, cyanine dyes and phycobiliproteins; the low valency carbohydrate binding ligand is labeled with a fluorophore and the glycoconjugate is labeled with a fluorophore in the non-radiative fluorescence resonance energy transfer process; low valency carbohydrate binding ligand is labeled with a fluorophore which is the acceptor and the glycoconjugate is labeled with a fluorophore which is the donor in the non-radiative fluorescence resonance energy transfer process.

In preferred embodiments, the first member of the specific binding pair is fluorophore-labeled low valency Concanavalin A, the second member of the specific binding pair is fluorophore-labeled glycosylated serum albumin capable of binding to low valency Concanavalin A, and the non-radiative fluorescence resonance energy transfer can be determined by measuring the ratio of the light emissions attributable to the two fluorophores.

In preferred embodiments, the specific binding pair is placed in a microdialysis vessel and then subcutaneously implanted in the subject; the specific binding pair is encapsulated and then subcutaneously implanted in the subject; the specific binding pair is mixed with a carrier, e.g., an oil into which glucose can pass and then implanted, e.g., injected subcutaneously, in the subject; the specific binding pair is tattooed into the skin of the subject; the components of the specific binding pair are chemically modified to enable them to bind to the cells of the subject; the specific binding pair is bound to a solid support which is then implanted in the subject, the support retaining the specific binding pair at the desired location once implanted in the subject; or at least one member of the specific binding pair is provided on a solid support, useful e.g., for repeatedly contacting body fluid samples; the specific binding pair is provided on a support having a membrane positioned thereon in such a manner that is covers the specific binding pair, the membrane having a pore size which prevents passage of the specific binding pair from the support to the body fluid but permits passage of carbohydrate between the body fluid and the support.

In preferred embodiments the sensor is encapsulated in an immunoisolating capsule or microcapsule. For example, the sensor can be encapsulated in a hydrogel core, e.g., an alginate or agarose core which core is surrounded by an immunoisolating membrane, e.g., a polyamino acid membrane, e.g., a polylysine membrane. Composite microcapsules of PCT/US96/03135 are particularly preferred for use with the sensors and methods described herein.

In preferred embodiments, the specific binding pair is illuminated, and the energy transfer is monitored, e.g., through the skin of the subject.

In preferred embodiments, an energy absorbing FRET donor component is coupled to a low valency carbohydrate binding ligand and an energy absorbing FRET acceptor is coupled to the glycoconjugate. In other preferred embodiments an energy absorbing FRET acceptor component is coupled to a low valency carbohydrate binding ligand and an energy absorbing FRET donor is coupled to the glycoconjugate.

The invention includes devices for evaluating a carbohydrate, e.g., glucose, in a sample, such as blood, urine, or extracellular fluid, either by in-vivo or in-vitro methods. The carbohydrate can be evaluated by placing the reactants described herein (e.g., a specific binding pair coupled to two energy absorbing FRET components) in contact with carbohydrate, e.g., glucose, present in a body fluid. For example, the reactants can be placed in, on, or under the skin, and glucose levels evaluated. The reactants can be introduced into an organ or vessel where they are exposed to glucose. In one embodiment the reactants are placed in, on or under the skin and glucose is evaluated by illuminating the skin at the excitation wavelength of the energy absorbing FRET donor. The energy transfer between the two energy absorbing FRET components is detected by a fluorimeter. The fluorimeter measures the ratio of fluorescence intensities at the two emission maxima wavelengths of the energy absorbing FRET components, or the quenching of the energy absorbing donor fluorescence at its emission maximum as a function of glucose concentration. Fluorescence can be measured with a filter based or a monochrometer based fluorimeter.

In-vivo methods of the invention can be modified to provide positive feedback to monitor changes in carbohydrate, e.g., glucose, levels. For example, in the case of glucose monitoring, if glucose levels are high, insulin is administered, e.g., by an implanted pump, to combat the deviation. In contrast, if glucose levels are low, a signal or alarm can be triggered to indicate an intake of glucose is required.

One in-vitro embodiment of this invention involves fixing the reactants on a solid support (e.g. stick) which is used to evaluate glucose in body fluid samples such as blood, urine, extracellular fluid by means of a fluorimeter.

A specific binding pair, as used herein, includes a first binding member and a second binding member. The first and second binding members can bind to one another in a reversible manner. The first binding member includes a low valency carbohydrate binding ligand, preferably coupled to an energy absorbing FRET component. The second binding member includes a carbohydrate, preferably coupled with a carrier molecule and an energy absorbing FRET component.

An energy absorbing FRET component, as used herein, is a substance that can either be a donor or an acceptor in the process of non-radiative energy transfer. Both the donor and the acceptor absorb energy. The function of the donor is to absorb energy at a first wavelength and transmit the absorbed energy via non-radiative energy transfer to the acceptor molecule. The function of the acceptor is to absorb the transmitted energy from the donor. The absorbed energy can be dissipated in a number of ways, for example, by emission of the energy at a second wavelength, dissipation as heat energy, or transfer of energy to the surroundings. Absorption by the acceptor can be measured by an acceptor parameter, e.g., sensitized acceptor emission or a donor parameter, e.g. donor fluorescence quenching. Requirements of the energy absorbing FRET components are that there is sufficient energy state overlap between the two in order for non-radiative energy transfer to occur. Furthermore, non-radiative energy transfer occurs only if the two are in close proximity (half energy transfer between a single donor and acceptor molecule occurs when the intermolecular distance is $R_0$).

An energy absorbing FRET donor, as used herein, is a substance that absorbs energy at a first wavelength. The absorbed energy creates an excited state in the donor. When the donor leaves the excited state, it can do so by emitting energy at the emission wavelength, dissipating the energy in the form of heat to its surroundings, or transmitting the absorbed energy via non-radiative energy transfer to an energy absorbing FRET acceptor.

An energy absorbing FRET acceptor, as used herein, is a substance that absorbs the non-radiative energy transferred from the energy absorbing FRET donor. The absorbed energy creates an excited state in the acceptor. When the acceptor leaves the excited state, it can do so by emitting the absorbed energy at a second wavelength, dissipating energy as heat, or transferring energy to the surroundings.

Specific, as used herein, describes the binding to a particular moiety with a higher affinity than related moieties. For example, a higher affinity binding to carbohydrates containing glucose or mannose compared to other carbohydrates which do not contain glucose or mannose.

Reversible, as used herein, describes an interaction that proceeds in either direction. For example, in a forward reaction the glycoconjugate binds to a low valency carbohydrate binding ligand and in the reverse reaction, the glycoconjugate is released from the low valency carbohydrate binding ligand. The reversible nature of the interaction should be maintained at the concentration at which a measurement is made and preferably over the concentration range at which the carbohydrate is to be measured, e.g. over the range of concentrations seen under physiological conditions.

Evaluating, as used herein, includes the detection of the presence or absence of a carbohydrate in a sample or the quantitative determination of the amount of the carbohydrate present in a sample.

Subject, as used herein, refers to a human or an experimental animal, e.g. a rodent, e.g. a mouse or rat, a dog, pig, cow, sheep, goat, or non-human primate. The subject can be one that suffers from a defect, e.g. a genetic or autoimmune defect, in carbohydrate metabolism.

Physiological concentration, as used herein, is the concentration of carbohydrate found in both normal and pathological states. For example, the physiological concentration of glucose refers to the range of glucose concentrations found in normal, hypoglycemic and hyperglycemic patients.

Determination of glucose concentration has applications in clinical settings for daily monitoring of glucose levels in individuals in whom glucose homeostasis is not maintained (e.g., in diabetes, hypoglycemia or hyperglycemia) and in addition to other biomedical research. Sensors of this invention are capable of detecting not only a broad range of glucose concentrations (e.g., from 0.05 mg/ml to 5.0 mg/ml or 0.5 to 5.00 mg/ml) but also a wide range of other carbohydrate concentrations.

Furthermore, the methods and devices described herein are not invasive, and do not involve rupturing the skin on a daily basis to make measurements. Invasive techniques are associated with a significant risk to patients developing serious infections. This is particularly true for diabetic patients who have a reduced resistance to infection.

The in-vivo sensors disclosed herein are a non-invasive after implantation. As the reactants do not aggregate and are not consumed, devices of the invention are reliable and reusable for extended periods, and significantly improves therapy for diabetic patients. Additionally, the devices described herein have a number of clinical and research applications evaluating other compounds and ligands, for example antibody-antigen interactions, receptor-ligand interactions, enzyme-substrate interactions.

Other features and advantages of the invention will be apparent from the following detailed description, and from the claims.

DETAILED DESCRIPTION

Proximity Based Signal Generating Methods

Proximity methods include those methods whereby a signal is generated when a first label moiety on the first member of the specific binding pair is brought into close proximity to a second label moiety on a second member of the specific binding pair. Examples of proximity methods include the following:

Fluorescence Resonance Energy Transfer (FRET)

The invention includes methods of evaluating a carbohydrate in a sample, (e.g., blood, urine, extracellular fluid) and devices useful in accomplishing carbohydrate evaluation. Methods of the invention rely on FRET to determine the extent of binding between members of a specific binding pair. Members of the specific binding pair are a glycoconjugate and a low valency carbohydrate binding ligand which binds reversibly to the glycoconjugate in competition with a carbohydrate analyte. Both the low valency carbohydrate binding ligand and the glycoconjugate are coupled to energy absorbing FRET components. Interaction between the specific binding pair results in the two energy absorbing FRET components being brought into the same vicinity. Non-radiative energy transfer between the two energy absorbing FRET components results in FRET. Carbohydrate analyte in the sample competes with the glycoconjugate for binding to the low valency carbohydrate ligand. Displacement of the glycoconjugate causes a decrease in FRET and allows evaluation of the analyte.

Once a molecule absorbs a photon of energy it enters an excited state, in order for the molecule to return to resting state the excess energy must be eliminated, by radiative or non-radiative processes. Radiative processes involve the direct emission of light in the form of fluorescence. Fluorescence as used herein, includes both fast fluorescence and phosphorescence. Non-radiative processes involve modes of exiting the excited state which do not involve direct emission of light by the donor. Non-radiative processes include dissipation of energy in the form of heat to the surroundings, use of the absorbed energy to promote chemical reactions, or transfer of energy to a neighboring molecule. The absorbing molecule enters an excited state and similarly eliminates the energy via radiative or non-radiative processes. Transfer of energy from one molecule to a second molecule occurs if there is sufficient energy state overlap and if the distance between the one energy absorbing donor and one energy absorbing acceptor is in the order of $R_0$, as defined below.

Figure 1:
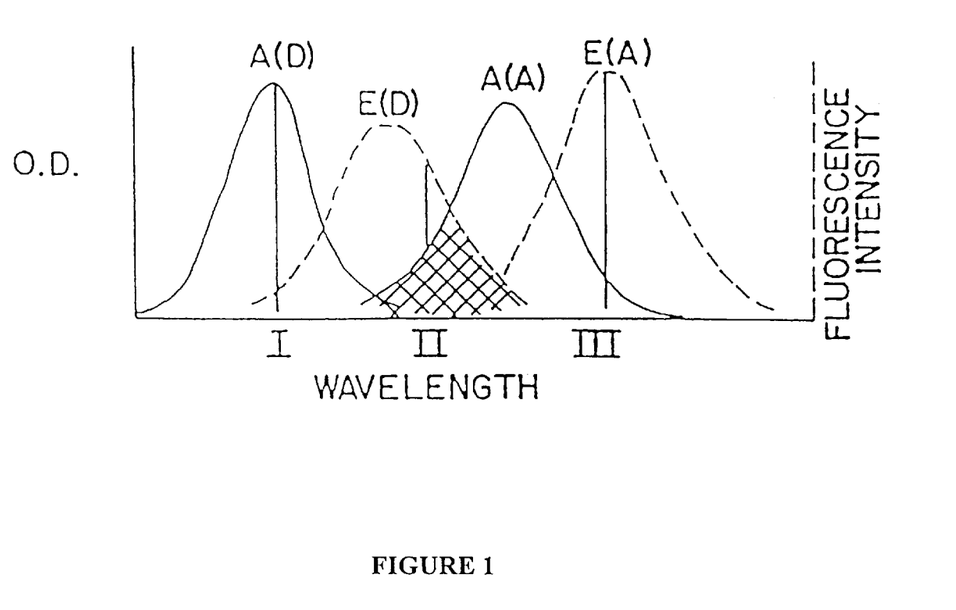
FIG. 1 A graph demonstrating the absorbance and emission spectra of an energy absorbing donor and an energy absorbing acceptor.

FRET is represented diagramatically in FIG. 1. The absorbance and emission of the energy absorbing donor is designated A(D), and E(D), respectively, and the absorbance and emission of the energy absorbing acceptor is designated A(A) and E(A), respectively. The area of energy state overlap between the donor emission and the acceptor absorbance is important in order for energy transfer to occur between the two components. The process of FRET involves illuminating a sample at a wavelength which excites the energy absorbing donor but not the not the energy absorbing acceptor or which excites the energy absorbing donor to a much greater extent than it does the energy absorbing acceptor. Excitation of the energy absorbing donor at wavelength I will result in energy being emitted at wavelength II, but not at wavelength III, the emission wavelength of the energy absorbing acceptor. Both the energy absorbing donor and the acceptor should absorb energy at one wavelength and emit the energy at a different wavelength.

FRET is an all or nothing quantum mechanical event, therefore, either the energy from an individual energy absorbing donor is transferred to an individual energy absorbing acceptor or it is not. Energy transfer only occurs when the absorption and emission spectra of the energy absorbing donor and energy absorbing acceptor overlap. When the energy absorbing acceptor (A) leaves its excited state, the emitted energy is rotated or depolarized with respect to the incident energy. As a result, FRET can be evidenced by a decrease in fluorescence intensity at II (i.e., decreased emission from the energy absorbing donor), an appearance of sensitized fluorescence intensity at III (i.e., an increased emission from the energy absorbing acceptor) and a depolarization of the fluorescence relative to the incident energy.

FRET also manifests itself in the lifetime in which the energy absorbing donor remains in an excited state. Typically, energy transfer shortens the lifetime of the energy absorbing donor. Fluorescence is an equilibrium process, the duration of which depends on the time the energy absorbing FRET component remains in an excited state. This is a result of competition between the rate at which the energy absorbing FRET component enters the excited state, driven by the incident energy, and the sum of the rates at which the energy absorbing FRET component leaves the excited state. Thus, the addition of an alternative mode of leaving the excited state, e.g., non-radiative energy transfer, shortens the lifetime of the energy absorbing FRET component.

Figure 2:
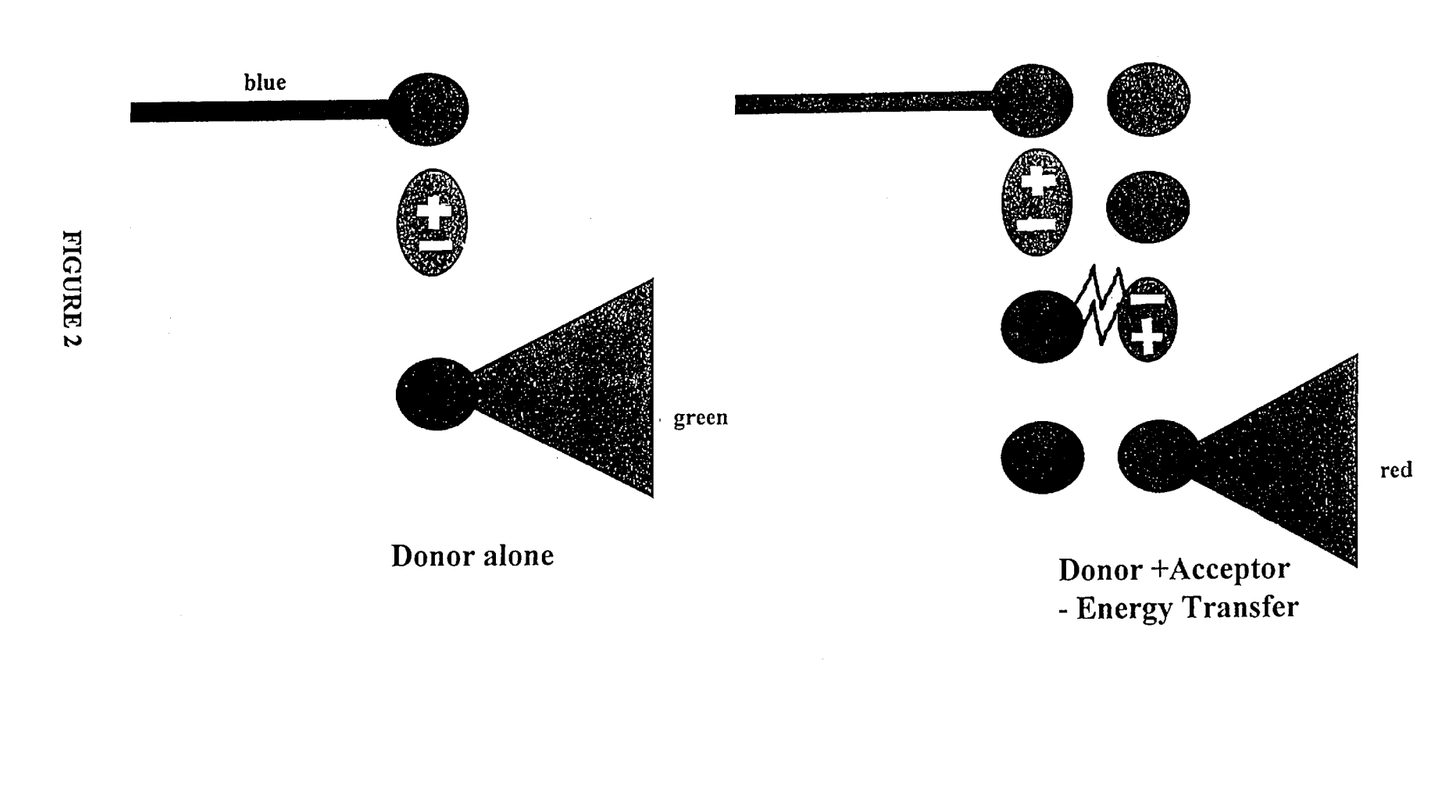
FIG. 2 A schematic illustration of non-radiative energy transfer between two energy absorbing FRET components.

A common form of non-radiative energy transfer is transfer between singlet states. Non-radiative energy transfer between two energy absorbing FRET components within the same vicinity is depicted in FIG. 2 An energy absorbing donor (D) absorbs a photon of energy that alters the charge distribution of the donor from a resting state to an excited state. The excited state charge distribution can be represented as a dipole where one side of the molecule becomes positively charged and the other side of the molecule becomes negatively charged. In addition to the emission of light, the energy absorbing donor molecule can return to its resting state by energy transfer from the energy absorbing donor to the energy absorbing acceptor (A), e.g., by inducing an opposite charged dipole in the energy absorbing acceptor molecule which consequently enters an excited state. A requisite for energy transfer, e.g., by dipole-induced dipole or energy transfer is that the energy absorbing acceptor is in the same vicinity as the energy absorbing donor. The energy absorbing acceptor can return to its resting state by emitting the absorbed energy at a different wavelength or non-radiative energy transfer.

In a FRET-based evaluation of an analyte, a sample or mixture can be illuminated at a wavelength which excites the energy absorbing donor but not the not the energy absorbing acceptor, or which excites the energy absorbing donor to a much greater extent that it does the energy absorbing acceptor. The sample is usually monitored at two separate wavelengths: that of energy absorbing donor emission wavelength and that of energy absorbing acceptor emission wavelength. If the energy absorbing donor and energy absorbing acceptor are not sufficiently close, FRET occurs minimally and emission only occurs at the energy absorbing donor wavelength. If however, the energy absorbing donor and energy absorbing acceptor are sufficiently close, FRET occurs. The results of this interaction can be a decrease in energy absorbing donor lifetime, a quenching of energy absorbing donor fluorescence, and an enhancement of the energy absorbing acceptor fluorescence intensity. The efficiency of energy transfer $E_f$, for a single energy absorbing donor and a single energy absorbing acceptor, falls off rapidly as the distance between a single energy absorbing donor and a single energy absorbing acceptor molecule, R, increases, the relationship is represented by the following equation:

$$E_f = 1/[1+(R/R_o)^6]$$

where R is the separation distance between energy absorbing donor and energy absorbing acceptor and $R_o$ is the distance for half transfer. $R_o$ is a value that depends upon the overlap integral of the energy absorbing donor emission spectrum and the energy absorbing acceptor excitation spectrum, that index of refraction, the quantum yield of the donor, and the orientation of the donor emission and the acceptor absorbance moments. Forster, T., *Z Natuforsch.* 4A, 321–327 (1949); Forster, T., *Disc. Faraday Soc.* 27, 7–17 (1959).

Fluorescene can be detected by time resolved techniques, such as gating pulse method, pulse method and phase modulation.

In the gating pulse method, the sample is excited with a brief pulse of energy and fluorescence is detected at a selected time period after the initial pulse. For example, if two fluorophores absorb energy and emit the absorbed energy in the form of fluorescence and one fluorophore has an fluorescence lifetime of 10 ns, while the second fluorophore has a fluoresence lifetime of 50 ns, it is possible to selectively detect the fluorescence from separate fluorophores. Detection at time 20 ns after the initial pulse of energy enables the detection of principally the fluorophore with the longer lifetime, i.e., the fluorophore with a fluoresence lifetime of 50 ns.

With the pulse method, the sample is excited with a brief pulse of energy and the time dependent decay of the fluorescence intensity is measured. For example, if the energy absorbing donor fluoresence decay is being measured, the rate of decay changes depending on energy transfer. If the energy absorbing donor transfers its energy to an energy absorbing acceptor via non-radiative energy transfer, the rate of the energy absorbing donor decay is faster than if the energy absorbing donor decays via radiative energy transfer.

Phase modulation is a method whereby the sample is excited with sinusoidal modulated energy and both the phase shift and amplitude of fluorescent light relative to the incident energy, is used to calculate the lifetime. For example, if the sample is excited with a light modulated sinusoidally at a specific frequency, due to the time lag between the absorption and emission, the emission is delayed in phase relative to the incident energy. This phase delay and amplitude modulation are used to calculate fluorescence lifetime.

Energy Absorbing FRET Components

An energy absorbing FRET component is a donor or an acceptor of non-radiative energy. Both donor and acceptor molecules absorb energy. The function of the donor molecule is to absorb energy at a first wavelength and transmit the absorbed energy via non-radiative energy transfer to the acceptor molecule. The function of the acceptor molecule is to absorb the transmitted energy from the donor molecule. Absorption allows for detection of energy transfer, e.g., by measurement of acceptor emission at a second wavelength. A requirement of the energy absorbing FRET components is that there is sufficient energy state overlap between the two molecules in order for non-radiative energy transfer to occur.

Preferred FRET components have the ability to absorb energy at a first wavelength and emit energy as fluorescence at a second wavelength. The FRET components should have energy state wavelengths in a range that avoid background interference from contaminants that may be present in the sample. Furthermore, the FRET components used in biological samples should have a fluorescence that is not quenched by water, since most biological measurements are made in an aqueous solution.

The relationship of energy absorbing donor and acceptor components is depicted in FIG. 1 and FIG. 2. The energy absorbing donor absorbs energy at a first wavelength and enters an excited state. When the energy absorbing donor leaves the excited state, it can transmit the energy via non-radiative energy transfer. If there is sufficient energy state overlap with the energy absorbing acceptor, the energy can be transferred from the energy absorbing donor to the energy absorbing acceptor. Subsequently, the energy absorbing acceptor enters an excited state by absorbing the energy from the energy absorbing donor. Preferred energy absorbing acceptors emit energy in the form of fluorescent light which is rotated or depolarized with respect to the incident energy resulting in FRET upon leaving the excited state. The diagrammatic representation in FIG. 1 depicts FRET as a decrease in fluorescence intensity at II (i.e., decreased emission from the energy absorbing donor), an appearance of fluorescence intensity at III (i.e., an increased emission from the energy absorbing acceptor) and a depolarization of the fluorescence relative to the incident energy.

A FRET component is coupled to each member of a specific binding pair, e.g., to a low valency carbohydrate binding ligand and a glycoconjugate. The interaction between the specific binding pairs is responsible for bringing the two energy absorbing FRET donor and acceptor components together. An interaction between the specific binding pair will bring the two energy absorbing FRET components together. Energy transfer will occur between the energy absorbing FRET donor and the energy absorbing FRET acceptor and FRET will be evidenced, e.g., in the form of decreased fluorescence intensity at II (i.e., decreased emission from the energy absorbing donor), an appearance of sensitized fluorescence intensity in III (i.e. increased emission from the energy absorbing acceptor) and depolarization of the fluorescence relative to the incident energy. In contrast, if there is no interaction between the specific binding pair will result in failure of the energy absorbing FRET donor and acceptor to come into sufficiently close proximity to allow efficient energy transfer. The presence of carbohydrate from a sample competes with the glycoconjugate for binding to the low valency carbohydrate binding ligand. Consequently, the binding site on the low valency carbohydrate binding ligand becomes occupied with the carbohydrate preventing the glycoconjugate from binding, resulting in failure of FRET.

Examples of suitable energy absorbing FRET components are fluorophores, e.g., NDB, dansyl, pyrene, anthracene, rhodamine, fluorescence and indocarbocyanine and their derivatives.

Examples of dyes useful as energy absorbing FRET donors/acceptor pairs include indocarbocyanine⇌indocarbocyanine, e.g, Cy3.5⇌Cy5.5, Cy5⇌Cy7, BODIPY (576/589)⇌BODIPY (650/665), fluorescein⇌rhodamine, NBD N-(7-nitrobenz-2-oxa-1, 3-diazol-3-yl)⇌rhodamine, fluorescein⇌eosin, fluorescein⇌erythrosin, dansyl⇌rhodamine, acridine orange⇌rhodamine, pyrene⇌fluorescein, 7-aminoactinomycin-D⇌fluorescein, 7-aminoactinomycin-D⇌R-phycoerythrin, fluorescein⇌R-phycoerythrin, ethidium monoazide⇌fluorescein, ethidium monoazide⇌R-phycoerythrin. Many of the above dyes are commercially available or can be synthesized using methods known to those skilled in the art.

Energy absorbing FRET components may be tested for suitability as energy absorbing FRET donors or acceptors using the FRET system described in U.S. Pat. No. 5,342,789. For example, substances can be evaluated using glucose as an analyte, Concanavalin A as the ligand, and glucose conjugated to BSA as the glycoconjugate. The energy absorbing donor or the energy absorbing acceptor component may be coupled to either the glycoconjugate or the ligand. If the energy absorbing donor component is coupled to the glycoconjugate then the energy absorbing acceptor component must be coupled to the ligand. If the energy absorbing acceptor component is coupled to the glycoconjugate then the energy absorbing donor component must be coupled to the ligand. The occurrence of FRET will be indicative of energy state overlap and non-radiative energy transfer between the two components. The level of FRET resulting from a combination of a pair of components should correspond to the glucose concentration in the sample. This can be tested by exposing the pair of components to a series of samples containing known concentrations of glucose. The resulting FRET response should correspond to the concentration of glucose.

Homogeneous time resolved fluorescence (HTRF)

Homogeneous time resolved fluorescence (HTRF) refers to a method of measuring constituents of a system without prior separation of the constituents from the system. The basic concept of HTRF is based on FRET whereby the interaction of two biomolecules e.g., a glycoconjugate and a reduced valency carbohydrate binding ligand each coupled a proximity based signal generating moiety e.g., to a donor and an acceptor fluorophore, can be measured by monitoring the fluorescence energy transfer from the excited donor fluorophore to the acceptor fluorophore when the two biomolecules are in proximity. The fluorescent signal from HTRF is measured after a time delay, thereby eliminating interfering signals.

Suitable examples of a donor fluorophore in HTRF include rare earth chelates or cryptates e.g., terbium, europium, dysprosium, samarium or neodynmium, preferably europium cryptate [(Eu)k]. Suitable examples of acceptor fluorophores in HTRF include allophycocyanin e.g., XL665, allophycocyanin B, phycocyanin C , phycocyanin R, or phthalocyanins.

The europium cryptate [(Eu)k] and XL665 FRET pair has several unique properties, for example, [(Eu)k] is stable within a pH range of 3 to 8, and has a long lifetime which enables conventional equipment to be used for measurement, e.g., a microplate fluorometer. Cryptate causes an enhancement of the $Eu^{3+}$ fluorophore which subsequently transfers the energy to XL665 when the two components are in close proximity. Cryptate also functions to protect $Eu^{3+}$ from fluorescence quenching. The acceptor molecule in HTRF, namely XL665, is a stabilized allophycocyanin molecule which accepts energy transferred from [(Eu)k].

Luminescent oxygen channeling assay (LOCI)

Luminescent oxygen channeling assay (LOCI) involves a photochemical reaction produced by the interaction of two proximity based signal generating label moiety components of the system. The first component, a photosensitizer generates singlet oxygen upon irradiation, e.g., a phthalocyanine containing photosensitizer. The second component is a photochemically activatable chemiluminescent compound, e.g., olefin, which reacts with the singlet oxygen to initiate a delayed luminescence emission.

Photosensitizers produce singlet oxygen upon irradiation, e.g., light irradiation. Examples of photoactivatable photosensitizers include, dyes and aromatic compounds. Examples of chemi-activated photosensitizers, include enzymes and metal salts. The photosensitizers compound should absorb energy, e.g. light, in the wavelength range of 200–1100 nm, and the lifetime of the excited state produced must be sufficiently long to permit energy transfer to oxygen. Examples of photosensitizers are described in N. J. Turro, "Molecular Photochemistry", page 132 W. A. Benjamin Inc., N. Y. 1965.

Photochemically activatable chemiluminescent compounds which undergo chemical reaction upon direct excitation with light, or by reaction with singlet oxygen, form a metabstable reaction product that decomposes with emission of light, usually within the wavelength range of 250–1200 nm. Most photochemically activatable chemiluminescent compounds will usually emit at wavelengths above 300–550 nm. Examples of photochemically activatable chemiluminescent compounds that react with singlet oxygen include olefins, e.g., enol ethers, enaminesdioxenes, arylimidazoles, luminol, luciferin and aquaphorin.

Low Valency Carbohydrate Binding Ligand

A low valency carbohydrate binding ligand, as used herein, is a ligand having the ability to bind, preferably reversibly, a carbohydrate. The ligand should bind, via a specific binding site or sites, the carbohydrate in a specific and reversible manner at concentration of the carbohydrate at which measurements are to be made. Valency refers to the number of carbohydrate binding sites, e.g., a valency of two refers to a species having two carbohydrate binding sites. The ligand should have as few carbohydrate binding sites as possible, preferably three or fewer. Such a ligand has reduced or low valency. In preferred embodiments the low valency carbohydrate binding ligand has a single carbohydrate binding site. In preferred embodiments the low valency carbohydrate binding ligand has a single carbohydrate binding site and is a monomeric molecule, e.g., a monomeric lectin molecule. If the low valency carbohydrate binding ligand is derived from a lectin or other naturally occurring molecule it will have at least one and preferably two fewer carbohydrate binding sites than the naturally occurring multimeric molecule. Such a ligand with reduced or low valency other than that derived from a lectin or other naturally occurring molecule will have three or fewer carbohydrate binding sites. Such a ligand has reduced or low valency, preferred low valency carbohydrate binding ligands are those which are derived from naturally occurring molecules, e.g., lectins.

The low valency carbohydrate binding ligand is one member of the specific binding pair and interacts with the carbohydrate coupled to the glycoconjugate, the second member of the specific binding pair. The low valency carbohydrate binding ligand is coupled to an energy absorbing FRET component. The energy absorbing FRET component may either be a donor or an acceptor of energy. If the energy absorbing FRET donor is coupled to the low valency carbohydrate binding ligand, then the energy absorbing FRET acceptor is coupled to the glycoconjugate. If the energy absorbing FRET acceptor is coupled to the low valency binding carbohydrate ligand, then the energy absorbing FRET donor is coupled to the glycoconjugate.

Interaction between the low valency binding carbohydrate ligand and the glycoconjugate brings the energy absorbing FRET components together permitting non-radiative energy transfer and FRET. In the presence of carbohydrate in the sample, there is competition between the glycoconjugate and the carbohydrate for binding to the low valency binding carbohydrate ligand. As the binding site (or sites) on the low valency carbohydrate binding ligand becomes occupied by carbohydrate molecules, glycoconjugate molecules are displaced or prevented from binding. This prevents the energy absorbing FRET components from moving together and failure to promote the energy transfer between the components.

Examples of carbohydrate binding ligands include a family of proteins called lectins. Lectins possess the ability to react reversibly with carbohydrates. The interaction is dependent on the lectin and the specificity of the lectin for particular carbohydrate moieties. Most lectins are oligomeric proteins, existing frequently as tetramers or dimers. Examples of lectins are shown in Table I.

TABLE I

Characteristics of Lectins

| Lectin | Carbohydrate Binding Sites | Polypeptides | Molecular Weight |
|---|---|---|---|
| Abrus precatorius agglutinin | 2 | α 33,000<br>β 36,000<br>$β_1$ 37,500 | 126,000–135,000 |
| Abrus precatorius toxin A | 1 | α 31,000<br>$α^1$ 32,500<br>β 35,500 | 60,000–62,500 |
| Abrus precatorius toxin C | 1 | α 29,000<br>β 36,000 | 64,000–66,600 |
| Adenia digitata (modeccin) | — | α 25,000–28,000<br>β 31,000–35,000 | 57,000–63,000 |
| Adenia digitata (modecin 6B) | — | α 27,000<br>β 31,000 | 57,000 |
| Aleuria aurantia | 2 | α 31,000 | 72,000 |
| Amphicarpaea bracteata | — | α 28,500<br>β 36,000<br>γ 32,000 | 135,000 |
| Anguilla anguilla | 2 | α 18,000–23,000 | 38,000–44,000 |
| Arachis hypogaea | $4^h$ | α 25,000–28,000 | 98,000–111,000 |
| Bauhinia purpurea | — | α 44,000 | 195,000 |
| Carcinoscorpius rotunda cauda | — | α 27,000<br>β 28,000 | 420,000 |
| Canavalia ensiformis | 4 | 26,500 | 106,000 |
| Crotalaria juncea | — | α 31,000 | 120,000 |
| Cytisus sessilfolius | — | — | 110,000 |
| Datura stramonium | 2 | α 40,000<br>β 46,000 | 86,000 |
| Dioclea grandiflora | — | α 25,000–26,000 | 100,000 |
| Dolichos biflorus | 2 | (II) α 27,300<br>(I) β 27,700 | 110,000–120,000 |
| Erythrina cristagalli | 2 | α 26,000<br>β 28,000 | 56,800 |
| Erythrina indica | 2 | α 30,000[kl]<br>β 33,000 | 66,000–68,000[kl] |
| Evonymus europaea | — | α 35,500 | 126,700 |
| Glycine max | 4 | α 30,000 | 120,000 |
| Griffonia simplicifolia I | — | α 32,000<br>β 33,000 | 114,000 |
| Griffonia simplicifolia II | 4 | α 30,000 | 113,000 |
| Griffonia simplicifolia IV | — | α 27,000<br>β 29,000 | 56,600 |
| Helix pomatia | 6 | α 13,000 | 79,000 |
| Hura crepitans (seeds, GalNAc) | — | α 31,000 | 120,000 |
| Lathyrus satiuus | — | α 4,400<br>β 19,000 | 49,000 |
| Lathyrus tingitarus | — | α 5,000<br>β 20,000 | 50,000 |
| Lens culinaris | | | |
| A | 2 | α 5,710<br>β 17,572 | 46,000 |
| B | | α 5,700<br>β 17,000 | 46,000 |
| Limax flavus | — | α 22,000 | 44,000 |
| Limulus polyphemus | — | α 18,000<br>β 24,000 | $(42,000)_{8-12}$ |
| Lotus tetragonolobus | | | |
| A | 4 | α 27,800 | 120,000 |
| B | 2 | α 27,000 | 58,000 |
| | 2 | α 27,800 | 117,000 |
| Lycopersicon esculentum A and B | — | α 71,000–74,000<br>α 10,000<br>β 12,000 | 71,000–74,000<br>40,000–46,000 |
| Macrotyloma axillare | — | α 10,000<br>β 12,000 | 108,000 |
| Momordica charantia | 2 | α 27,000–29,000<br>β 30,000–36,000 | 115,000–129,000 |

TABLE I-continued

Characteristics of Lectins

| Lectin | Carbohydrate Binding Sites | Polypeptides | Molecular Weight |
|---|---|---|---|
| Onobrychis vicilifolia | — | α 26,509 | 53,000 |
| Oryza sativa | 4 | α 18,000–19,000 | 38,000 |
| Pisum sativum | | | |
| A (I) | 2 | α 5,753 | 50,000 |
| | | β 17,000 | |
| B (II) | | α$^1$ 5,700 | 50,000 |
| | | β 17,000 | |
| Phaseolus lunatus | 1/chain | α 31,000 | (62,000)$_{2-4}$ |
| | | α$^1$ 31,000 | |
| | | β 31,000 | |
| Phaseolus vulgaris | — | α 31,000 | 126,000 |
| | | β 17,000 | |
| | — | 150,000 | E$_4$ |
| Phytolacca americana | | | |
| Pa-1 | — | α 22,000 | (22,000)$_n$ |
| Pa-2 | | α 28,000–31,000 | 28,000–30,000 |
| Pa-3 | | α 25,000 | 25,000 |
| Pa-4 | | α 21,000 | |
| Pa-5 | | α 19,000 | |
| Psophcarpus tetragonolobus | | | |
| B1 | — | α 29,000 | 58,000 |
| B2 | | β 29,000 | 58,000 |
| B3 | | γ 29,000 | 58,000 |
| Ricinus communis agglutinin | 4 | α 29,500–33,000 | 120,000 |
| | | β 34,000 | |
| Ricinus communis toxin | 2 | α 29,500–31,000 | 63,000 |
| | | β 34,000 | |
| Solanum tuberosum | 2 | α 50,000 | 100,000 |
| Sophora japonica | — | α 32,500 | 132,800 |
| | | β 32,500 | |
| Triticum vulgaris | 4(2)2 | α 21,600 | 43,200 |
| Ulex europeus I | — | α 29,000 | 60,000–68,000 |
| | | β 31,000 | |
| Ulex europeus II | — | α 23,000–25,000 | 105,000 |
| Vicia cracca (Man) | 2 | α 5,759 | 44,000 |
| | | β 17,500 | |
| Vicia cracca | | | |
| I (GalNAc) | — | α 33,000 | 114,000 |
| II (GalNAc) | — | | 125,000 |
| Vicia ervilia | — | α 4,700 | 53,000 |
| | | β 21,000 | |
| Vicia faba | 2 | α 5,571 | 52,542 |
| | | β 20,700 | |
| Vicia sativa | — | α 6,000 | 40,000 |
| | | β 14,000 | |
| Vicia graminea | — | α 26,000 | 105,000 |
| Vicia villosa | | | |
| A$_4$ | — | α 33,600 | 110,000–120,000 |
| A$_3$B | | β 21,000 | |
| A$_2$B$_2$ | | | 94,000 |
| AB$_3$ | | | |
| B$_4$ | | | 108,000 |
| Viscus album (lectin II viscumin) | — | α 29,000 | 60,000 |
| | | β 34,000 | |
| Wistaria floribunda agglutinin | 1/chain | α 28,000–32,000 | (60,000)$_{1-4}$ |
| Wistaria floribunda mitogen | — | α 32,000 | 66,000 |

Examples of some naturally occurring lectins with a valency less than four are shown in boldface in Table I and include *Lens culinaris* A, *Pisum sativatum* A (I), *Vicia cracca* and *Vicia faba, Wistaria floribunda* (Irwin et al, 1986, The lectins, Academic Press, Inc.). These lectins have a specificity for glucose and mannose and can be tested for suitability as members of the specific binding pair as described below.

A low valency carbohydrate binding ligand can be generated from an oligomeric protein, by modification (inactivation) of a binding site, or by reducing the number of carbohydrate binding site containing subunits in the molecule. For example, , a tetramer can be converted to a dimer or a monomer, e.g., by the application of chemical or photolabelling techniques. Such molecules are referred to herein as "subunit reduced molecules". Thus, preferred low valency carbohydrate binding ligands include subunit reduced molecules, e.g. lectins. Preferred reduced valency lectins are monovalent monomeric lectins, e.g. monomeric Concanavalin A.

Concanavalin A, a multivalent member of the lectin family, can be provided in a subunit reduced form. At physiological pH, Concanavalin A consists largely of tetrameters, whereas below pH 6.0, the tetrameter dissociates to form dimers (Wang et al., (1975) *J. Biol. Chem.* 250: 1490–1502).

Procedures for preparing reduced valency Concanavalin A or reduced valency Concanavalin A derivatives are known in the art. For example, chemical modification procedures can be used to dissociate native Concanavalin A into dimeric molecules. The method of Gunther et al., (1973), *PNAS*, 70:1012–1016 describes succinylation of Concanavalin A by reacting Concanavalin A with succinic anhydride. This reaction produces the succinyl derivative of Concanavalin A (succinyl Concanavalin A) which exists as a divalent dimer under physiological conditions.

A monovalent monomer of Concanavalin A can be generated using the method of Tanaka et al., (1981), *J. Biochem,* 98:1643–1646. The method involves a photochemical reaction using tetrameric Concanavalin A with chloroacetamide and methyl-α-D-mannopyranoside followed by irradiation with a high pressure vapor mercury lamp. This reaction induces alkylation at one or two tryptophan residues per subunit of Concanavalin A and is responsible for the dissociation of tetrameric Concanavalin A into monovalent monomers that are stable at physiological pH.

Photoaffinity labelling reaction whereby native Concanavalin A is labelled with p-azidophenyl-α-D-mannopyranoside, and treated with hydroquinone under ultraviolet (U.V.) radiation is described by Beppu et al., (1975), *J. Biochem.* 78:1013–1019. The labelled Concanavalin A derivative produced exists as a monovalent dimer at a pH 5.0, but dimerises into a divalent tetramer at pH 7.0.

Monovalent derivatives of Concanavalin A can also be generated by a combination of both chemical and photoaffinity labelling techniques. For example, the preparation of monovalent succinyl-Concanavalin A is described as follows: The native Concanavalin A tetramer is converted to a dimeric succinyl-Concanavalin A Concanavalin A derivative by reacting native Concanavalin A with succinic anhydrid, Gunther et al., 1973, *PNAS,* 70, 1012–1016. The resulting succinyl-Concanavalin A is used as a starting material for photoaffinity labelling with p-azidophenyl-α-D-mannopyranoside, and hydroquinone followed by UV irradiation generating monovalent succinyl-Concanavalin A, Beppu et al., 1976, *J. Biochem.* 79:1113–1117.

The method of Fraser et al., 1976, *PNAS,* 73:790–794 describe the production of the monovalent derivatives of Concanavalin A by slight modifications of the chemical and photoaffinity labelling procedure. For example, by twice succinylation or acetylation of native Concanavalin A followed by U.V. irradiation of the succinyl-Concanavalin A derivative or the acetyl-Concanavalin A derivative in the presence of p-azidophenyl-α-D-mannopyranoside and hydroquinone. This reaction generates monomeric succinyl-Concanavalin A or monomeric acetyl-Concanavalin A, respectively. The same methodology may be used to generate other monovalent Concanavalin A derivatives.

Monovalent forms of Concanavalin A have also been prepared by proteolytic digestion of metal deficient Concanavalin A using pepsin and trypsin Wands et al., (1976) PNAS, 73:2118–2122 or with chymotrypsin, Thomasson et al., (1975), 67:1545–1552.

Candidate low valency carbohydrate binding ligands may be tested using the FRET system described in U.S. Pat. No. 5,342,789. For example, a candidate low valency carbohydrate binding ligand can be evaluated using a carbohydrate, e.g., glucose as analyte and the sugar conjugated to BSA as the glycoconjugate. Energy absorbing FRET components such as the fluorescent dyes, rhodamine and fluorescein may be coupled to the specific binding pair. The occurrence of FRET is indicative of an interaction between the low valency carbohydrate binding ligand and the glycoconjugate, resulting in the energy absorbing FRET components being brought into the close proximity and successful energy transfer.

For accurate assessment of an interaction between the low valency carbohydrate binding ligand and the glycoconjugate, the carbohydrate conjugated on the glycoconjugate should be selected based on the specificity of the low valency carbohydrate binding ligand. For example to test the interaction of divalent succinyl-Concanavalin A as a low valency binding ligand, glucose or mannose should be the carbohydrate conjugated to the glycoconjugate, since Concanavalin A is known to have a high affinity for both. Therefore, suitable specific binding pairs which are useful not only for evaluating glucose but also have other implications for investigating the presence and concentration of other carbohydrates are disclosed herein.

Figure 3:
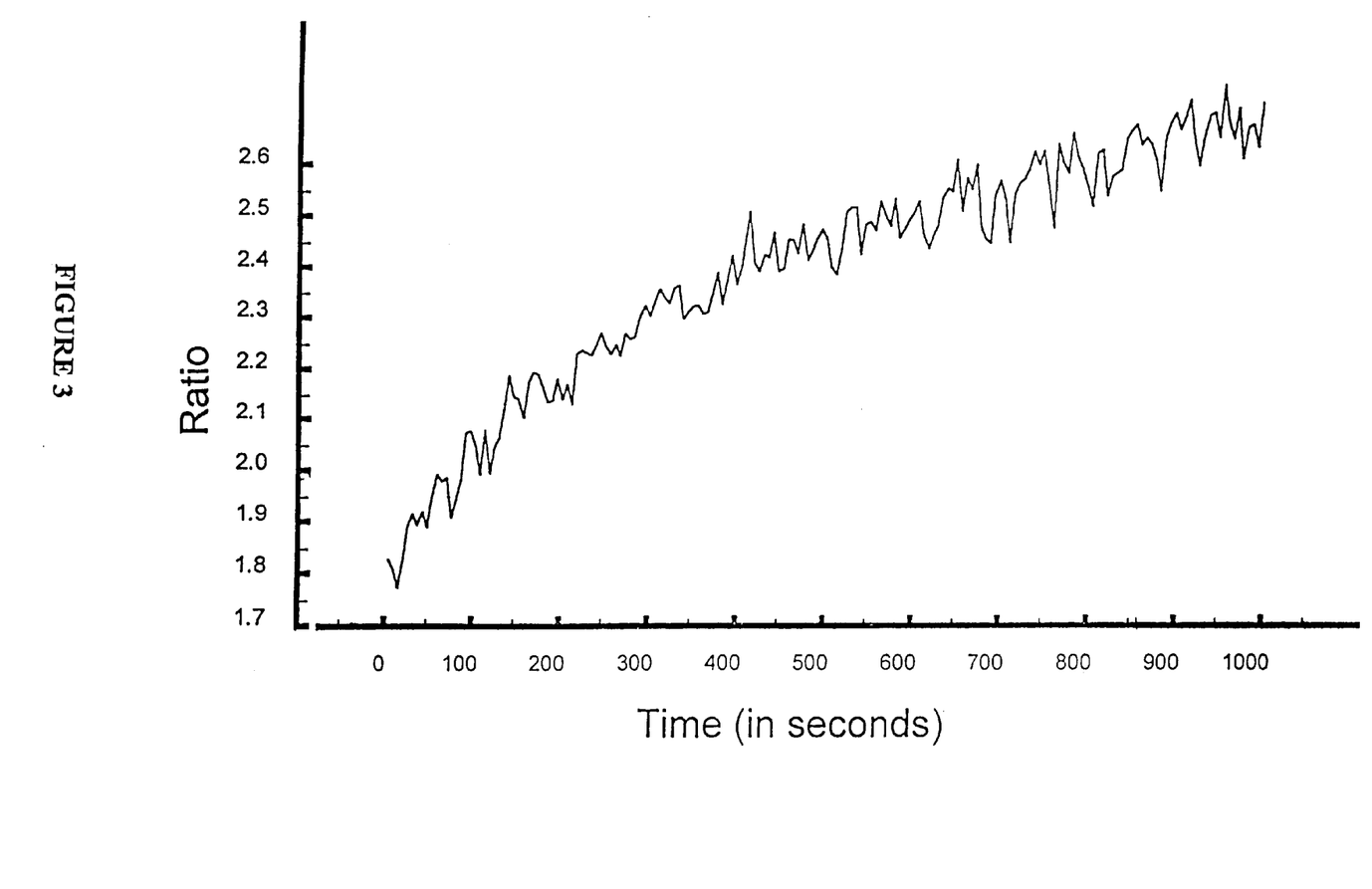
FIG. 3 A graph demonstrating the binding kinetics of monovalent Concanavalin A.

The reversal of binding kinetics of monovalent Concanavalin A for a glycoconjugate is depicted in FIG. 3. Fluorescent dyes Cy5 and Cy7 were used as the energy absorbing FRET components. The glycoconjugate was coupled to Cy5 while the monovalent Concanavalin A was coupled to Cy7. The specific binding pairs were incubated in the presence of 500 mg/dL glucose solution. As FRET decreases by the competitive binding of glucose to the Concanavalin A, the emission ratio of Cy5/Cy7 increases. At time zero, the single binding site of monovalent Concanavalin A is occupied by the glycoconjugate, therefore the Cy5 and Cy7 dyes are close together enabling non-radiative energy transfer and a high probability of FRET. Over time, the analyte glucose competitively inhibits binding of the glycoconjugate to monovalent Concanavalin A. A reduction in FRET and an increase in the emission ratio of Cy5/Cy7 is consequently observed.

Figure 4:
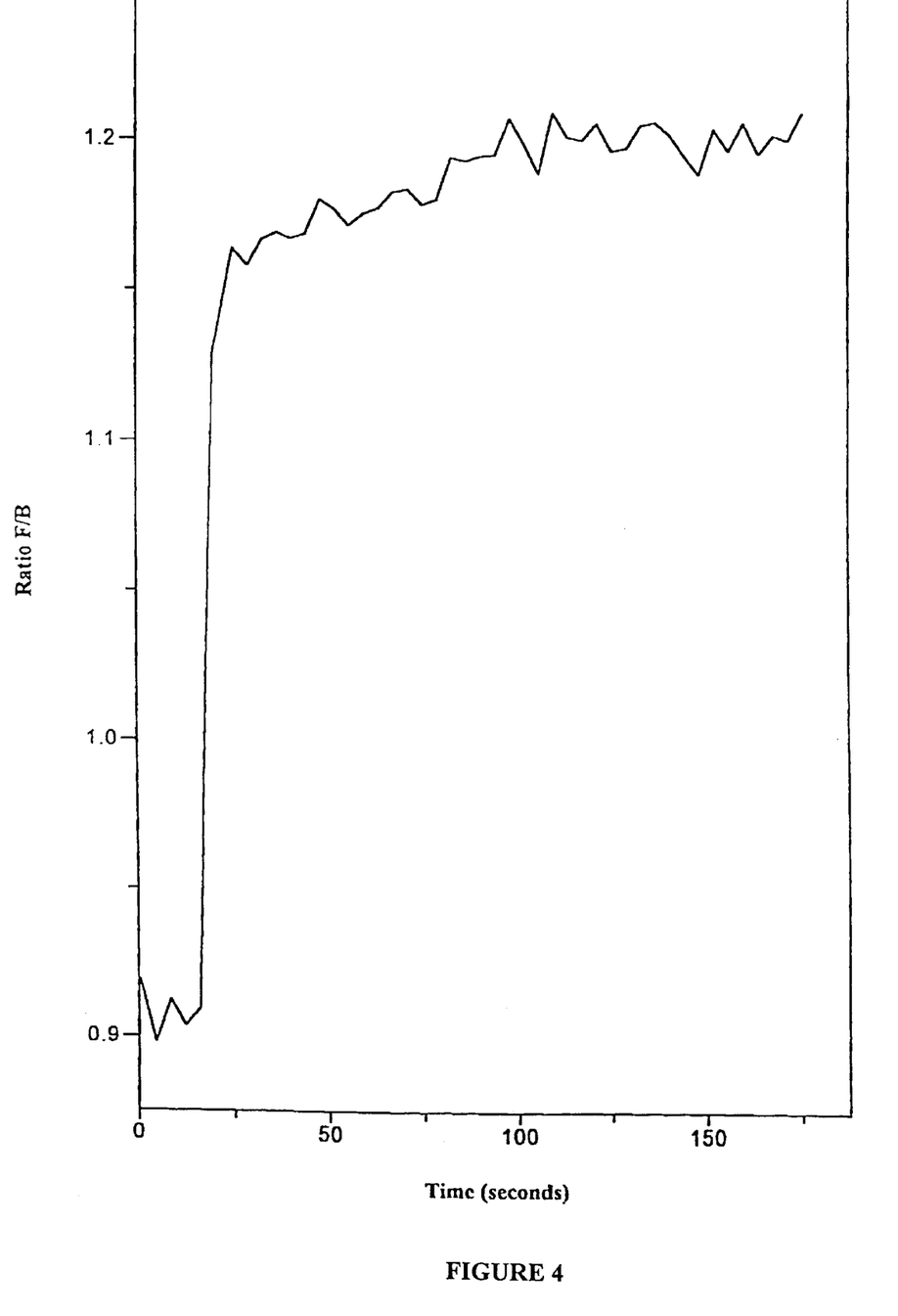
FIG. 4 A graph demonstrating the binding kinetics of divalent succinyl-Concanavalin A.

Similar kinetic binding studies were conducted using divalent succinylated Concanavalin A, shown in FIG. 4. In this experiment, Fluorescein is coupled to glycosylated bovine serum albumin (FGB) and BODIPY is coupled succinyl-Concanavalin A. The kinetic profiles of the graph is similar to those of monovalent Concanavalin A, demonstrating that over a period of time the two binding sites of divalent Concanavalin A become occupied by glucose in a competitive manner.

Reduced valency ligands are advantageous in that a lower number of binding sites reduces aggregation. The glucose analyte need only compete with a minimal number of glycoconjugates from each reduced valency Concanavalin A. This improves the performance and sensitivity of the FRET system.

Glyconjugate

A glycoconjugate, as described herein, includes a carbohydrate, a label, e.g., a FRET component, and, preferably, a carrier molecule. The carbohydrate should be the same as the analyte. In FRET-based applications the label is a FRET component. In preferred embodiments the carbohydrate and the FRET component are both bound to a carrier molecule. The glycoconjugate binds specifically and reversibly to a low valency carbohydrate binding ligand.

A glycoconjugate is one member of the specific binding pair. It binds reversibly with the low valency carbohydrate binding ligand, the second member of the specific binding pair. An energy absorbing FRET component is coupled to the glycoconjugate and can either be a donor or an acceptor of energy. If the energy absorbing FRET donor is coupled to the glycoconjugate, then the energy absorbing FRET acceptor is coupled to the low valency carbohydrate binding ligand. If the energy absorbing FRET acceptor is coupled to the conjugate, then the energy absorbing FRET donor is coupled to the low valency binding carbohydrate ligand.

The analyte carbohydrate should competitively inhibit binding of the glycoconjugate to the low valency carbohydrate binding ligand. Examples include carbohydrates such as glucose, fructose, sucrose, mannose, monosaccharides and oligosaccharides.

The carrier molecule (when present) should be nonreactive with substances found in the sample, provide a site at which a carbohydrate can be bound, and provide a site at which a FRET component can be bound. Furthermore, the carrier molecule should not interfere with the binding between the conjugated carbohydrate and the low valency carbohydrate binding ligand. Suitable carriers include proteins, such as bovine, or human serum albumin, β-lactoglobulin, immunoglobulins, antibodies, glycoproteins or glycolipids containing the carbohydrate moiety recognised by the low valency carbohydrate binding ligand; and synthetic polymers to which the carbohydrate is covalently coupled. Methods of coupling FRET components to carrier molecules are known to those skilled in the art and incorporated herein by reference (Hermanson, 1996, Bioconjugate Techniques, Academic Press, Inc).

A glycoconjugate can be tested for suitability using the FRET system described in U.S. Pat. No. 5,342,789. For example, a candidate glycoconjugate can be tested using glucose as the analyte and FRET labelled Concanavalin A as one member of the specific binding pair. Rhodamine and fluorescein can be used as the energy absorbing FRET components. Upon an interaction between the glycoconjugate and the Concanavalin A energy transfer between the energy absorbing FRET components will result in FRET. However, if there is no interaction between the glycoconjugate and the Concanavalin A, the energy absorbing FRET components will not be within a suitable distance for energy transfer and FRET will not occur.

FRET-based Measurement of Glucose Concentrations

Figure 5:
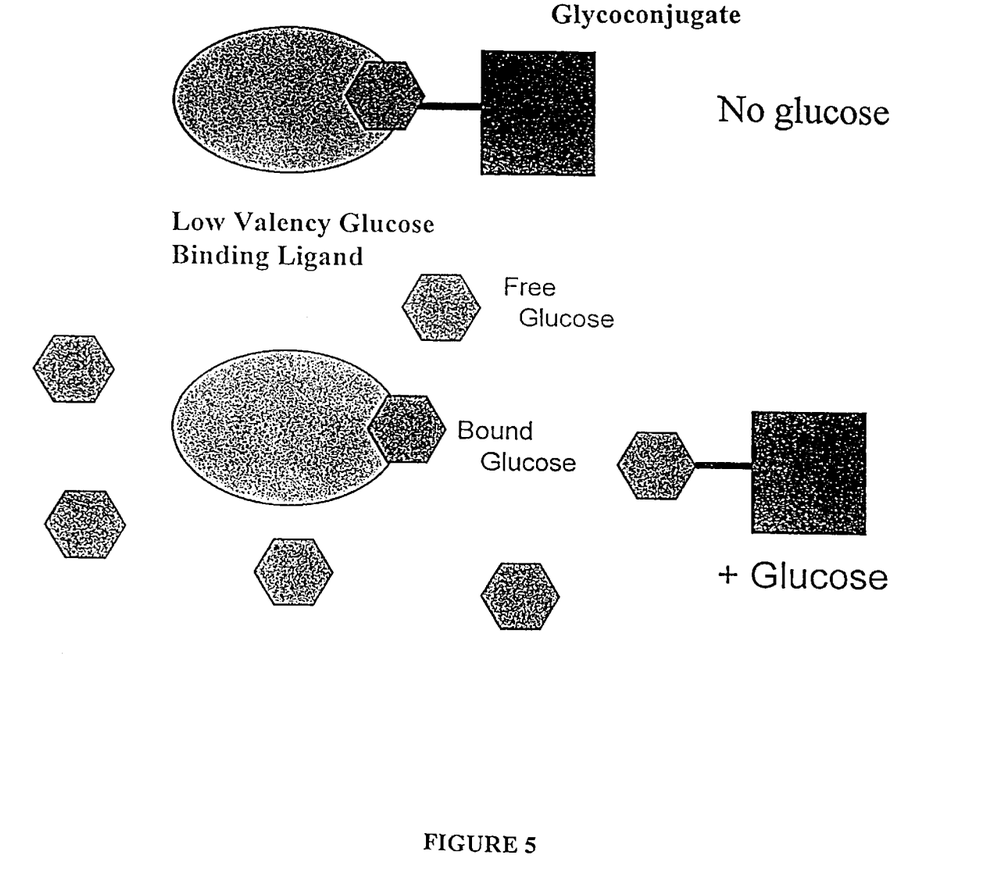
FIG. 5 A schematic illustration of reversible binding between the specific binding pairs in the presence of glucose.

Glucose measurements using the low valency carbohydrate binding ligand and the glycoconjugate is based on reversible binding of the low valency carbohydrate binding ligand to free glucose or the glycoconjugate, as depicted in FIG. 5. In the absence of glucose, the glycoconjugate occupies the binding site on the low valency carbohydrate binding ligand. In the presence of glucose, the glycoconjugate is displaced and the binding site occupied by glucose.

Figure 6:
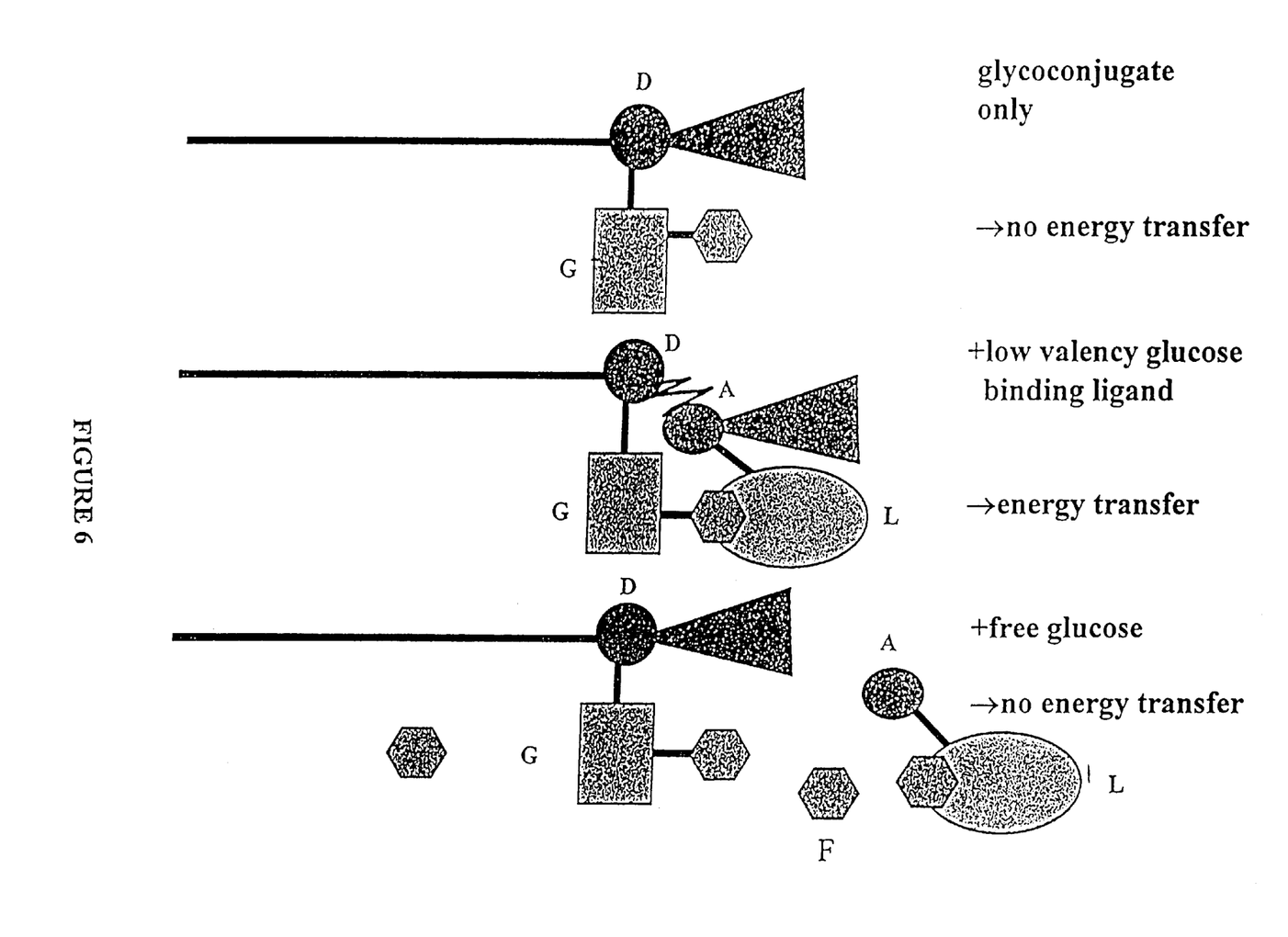
FIG. 6 A schematic illustration of the use of FRET to evaluate glucose.

The use of FRET to measure glucose concentrations in solution is represented diagrammatically in FIG. 6. The specific binding pair includes a glycoconjugate (G) having glucose conjugated to a carrier molecule and having a covalently coupled energy absorbing FRET component, such as a fluororphore. The second binding member is a low valency glucose binding ligand (L) with a high specificity for glucose (e.g., reduced valency Concanavalin A, or reduced valency Concanavalin A derivatives), covalently coupled to an energy absorbing FRET component, such as a fluororphore. The energy absorbing FRET component on the glycoconjugate is generally not the same energy absorbing FRET component on the low valency glucose binding ligand.

One of the energy absorbing FRET component is an energy absorbing FRET donor (D) and the other an energy absorbing FRET acceptor (A). For the purposes of this illustration, the energy absorbing FRET donor (D) has been placed on the glycoconjugate (G) and the energy absorbing FRET acceptor (A) has been placed on the low valency glucose binding ligand (L). The association between the specific binding pair is shown below:

where DG represents the energy absorbing donor-glucose complex, AL represents the energy absorbing acceptor-low valency glucose binding ligand, and DG-LA represents the association between the glucose from the glycoconjugate and the low valency glucose binding. Upon association, the two members of the specific binding pair are close enough to allow energy transfer between the energy absorbing FRET donor and the energy absorbing FRET acceptor.

The presence of free glucose (F) introduces a competitive inhibitor into the formula because free glucose competes with the conjugated glucose for the low valency glucose binding ligand. The concentration of glucose has an inverse proportional relationship with the low valency glucose binding ligands available for glycoconjugate binding. Thus, increasing the glucose concentration decreases the number of low valency glucose binding ligands available for the glycoconjugate binding since the binding site (or sites) of the low valency glucose binding ligand become occupied with glucose. At relatively low concentrations of glucose, the non-radiative energy transfer efficiency between the energy absorbing FRET components will remain high because the interaction between the specific binding pairs is not significantly affected. In contrast, at high concentrations of glucose, the non-radiative energy transfer efficiency between the energy absorbing FRET components will be low, because glucose successfully competes the low valency glucose binding ligand away from the glycoconjugate. Thus it is possible to obtain a reliable, repeatable evaluation of glucose in a sample.

The methods of the invention are useful for evaluating glucose concentrations over a physiological range that includes that found in normal individuals, and those individuals with a glucose imbalance (i.e., patients with diabetes, hyperglycemia or hypoglycemia). The range of evaluation includes glucose concentrations from 0.05 mg/ml to 5.0 mg/ml or 0.5 mg/ml to 5.0 mg/ml. Measurements are made using an appropriate volume of sample from an individual (e.g., 10–100 $\mu$l), and the reactants are stable and reusable.

Various devices that are suitable for the detection of glucose concentration in blood either by in-vivo or in-vitro methods are within the invention. These devices can remain active for extended period of time (e.g., one, two, or six months or more) before having to be replaced.

In-vivo embodiments provide for the cutaneous measurement of glucose by placing the reactants (i.e., the specific binding pair coupled to the energy absorbing FRET components) in contact with glucose. The reactants can be placed in, on, or under the skin. Alternatively, the reactants can be placed within an organ or a vessel (e.g., a vein or artery) where they are in exposed to the glucose in the body. In one embodiment, reactants are placed in, on or under the skin, and can, e.g., be monitored for glucose by illuminating the skin at a wavelength that excites the energy absorbing donor. The absorbed energy is transferred to an energy absorbing acceptor and FRET evaluated e.g., by measuring the emission maxima wavelength for the two energy absorbing FRET components. By way of example, if fluorescein and BODIPY are used as the energy absorbing FRET donor and the energy absorbing FRET acceptor, respectively, the fluorescent intensities are measured at 520 nm and 590 nm, $FI_{520}$ and $FI_{590}$, respectively (corresponding to the respective emission maxima wavelengths of these fluorescent dyes). The measure of energy transfer and the efficiency of energy transfer between the fluorescent dyes is detected by a fluorimeter. The ratio of fluorescence intensities at the two emission maxima wavelengths (e.g., $FI_{520}/FI_{590}$) or the quenching of the energy absorbing donor fluorescence (e.g., fluorescein) at its emission maximum as a function of glucose concentration is measured.

The reactants can be introduced into the body within a support material that retains the reactants at a desired location. For example, the reactants can be encapsulated in a microdialysis vessel or in microcapsules with a diameter of about 1 mm 50–100 mm. The encapsulated glucose sensor can be implanted intracutaneously in the body. In another procedure, reactants may be mixed with a carrier, e.g., silicone or fluorocarbon oils, and injected subcutaneously. The reactants may also be tattooed onto the skin or contained within a transcutaneous patch. Alternatively, the reactants may be modified in such a way that when injected subcutaneously, they become bound to cell structure and remain fixed in situ under the skin. For example, the albumin of the glycoconjugate can be engineered to include a reactive group that binds cells.

Any in vivo device that exposes the reactants to glucose can be modified to include an insulin pump. The pump can inject insulin into a patient upon detection of inappropriately high glucose levels.

In in vitro embodiments of the invention include exposing the reactants to a sample of blood or other bodily fluids containing glucose (e.g., urine, extracellular fluid) that has been removed from the body. Glucose is detected and quantified by exposing the reactants in with the glucose-containing bodily fluid in a fluorimeter.

In one embodiment, the reactants may be adhered to a solid substrate (e.g., a stick) or may be contained in a chamber (e.g., a microdialysis vessel). The reactants may also be contained in a pen cartridge that dispenses an appropriate volume of the reactants into the blood or other bodily substance containing glucose.

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of evaluating a carbohydrate in a sample comprising:
   a) contacting the sample with a specific binding pair which comprises a first binding member and a second binding member;
      wherein the first binding member comprises a low valency carbohydrate binding ligand coupled to a first energy absorbing material, said low valency carbohydrate binding ligand having no greater than three carbohydrate binding sites, wherein the second binding member is a glycoconjugate which comprises a carbohydrate moiety and a second energy absorbing material;

wherein the excited state energy level of the first energy absorbing material overlaps with the excited state energy level of the second energy absorbing material; and wherein the low valency carbohydrate binding ligand and the glycoconjugate reversibly bind to each other such that carbohydrate present in the sample displaces the glycoconjugate and reversibly binds to the low valency carbohydrate binding ligand; and b) evaluating the extent to which non-radiative fluorescence resonance energy transfer occurs between the first energy absorbing material and the second energy absorbing material, thereby evaluating the carbohydrate in the sample.

2. The method of claim 1, wherein the method further comprises comparing the result of step (b) with the relationship between (1) the extent of non-radiative energy transfer between the first energy absorbing material and the second energy absorbing material and (2) carbohydrate presence obtained from a calibration step.

3. The method of claim 1, wherein detection comprises the use of a proximity-based sigal generatig moiety.

4. The method of claim 1, wherein the sample is selected from the group consisting of a urine sample, a blood sample, a plasma sample, intracellular fluid, interstitial fluid, and a cell homogenate or extract.

5. The method of claim 1, wherein the carbohydrate is selected from the group consisting of a monosaccharide, a disaccharide, a polysaccharide, glucose, and a carbohydrate moiety of a molecule or a supramolecular structure.

6. The method of claim 1, wherein the glycoconjugate is a glycosylated serum albumin.

7. The method of claim 1, wherein the low valency carbohydrate binding ligand is a lectin.

8. The method of claim 1, wherein the low valency carbohydrate binding ligand is reduced valency Concanavalin A having no greater than three carbohydrate binding sites.

9. The method of claim 8 wherein said reduced valency Concanavalin A has one carbohydrate binding site.

10. The method of claim 1, wherein the low valency carbohydrate binding ligand and the glycoconjugate bind reversibly over the range of carbohydrate concentrations found in body fluids.

11. The method of claim 1, wherein the first and second energy absorbing materials are fluorophores.

12. The method of claim 1, wherein, the first member of the specific binding pair is low valency Concanavalin A having no greater than three carbohydrate binding sites labeled with a first fluorophore wherein said first fluorophore emits a fluorescence signal at a first wavelength upon illumination;

the second member of the specific binding pair is glycosylated serum albumin labeled with a second fluorophore wherein said second fluorophore emits a fluorescence signal at a second wavelength upon illumination; and the extent of non-radiative fluorescence resonance energy transfer is determined by measuring the ratio of said fluorescence signal emitted by said first fluorophore to said fluorescence signal emitted by said second fluorophore.

13. The method of claim 12 wherein said low valency Concanavalin A has one carbohydrate binding site.

14. The method of claim 1, wherein the specific binding pair is encapsulated in an inununoisolating capsule or microcapsule.

15. The method of claim 1, wherein the specific binding pair is illuminated, and the energy transfer is monitored.

16. The method of claim 1, wherein the first energy absorbing material is a donor material which is coupled to the low valency carbohydrate binding ligand and the second energy absorbing material is an acceptor material which is coupled to the glycoconjugate.

17. The method of claim 1, wherein the first energy absorbing material is an acceptor material which is coupled to the low valency carbohydrate binding ligand and the second energy absorbing material is a donor material which is coupled to the glycoconjugate.

* * * * *